United States Patent
Sakai et al.

(10) Patent No.: US 7,368,602 B2
(45) Date of Patent: May 6, 2008

(54) PROCESS FOR PRODUCING (METH) ACRYLIC ACID

(75) Inventors: Toyofumi Sakai, Himeji (JP); Naoki Serata, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/655,113

(22) Filed: Jan. 19, 2007

(65) Prior Publication Data

US 2007/0173667 A1    Jul. 26, 2007

(30) Foreign Application Priority Data

Jan. 20, 2006    (JP)    ............... 2006-013204

(51) Int. Cl.
*C07C 51/42*    (2006.01)
(52) U.S. Cl. .................................... 562/600
(58) Field of Classification Search ................ 562/600
See application file for complete search history.

(56) References Cited

U.S. PATENT DOCUMENTS

| | | |
|---|---|---|
| 3,621,664 A | 11/1971 | Saxer |
| 6,252,110 B1 | 6/2001 | Uemura et al. |
| 6,395,140 B1 | 5/2002 | Herbst et al. |
| 6,498,272 B1 | 12/2002 | Schröder et al. |
| 6,555,707 B1 | 4/2003 | Nestler et al. |
| 6,646,161 B1 | 11/2003 | Eck et al. |
| 7,183,428 B2 * | 2/2007 | Ueno et al. ............ 562/545 |
| 2004/0015014 A1 | 1/2004 | Nishimura et al. |
| 2004/0249200 A1 | 12/2004 | Serata et al. |
| 2004/0249201 A1 | 12/2004 | Ueno et al. |
| 2005/0171380 A1 | 8/2005 | Bub et al. |

FOREIGN PATENT DOCUMENTS

| | | |
|---|---|---|
| EP | 1 116 709 | 7/2001 |
| EP | 1 484 310 | 12/2004 |
| GB | 1 350 736 | 4/1974 |
| JP | 53-41637 | 11/1978 |
| JP | 11-12222 | 1/1999 |
| JP | 2001-516737 | 10/2001 |
| JP | 2001-520213 | 10/2001 |
| JP | 2001-348358 | 12/2001 |
| JP | 2001-348359 | 12/2001 |
| JP | 2001-348360 | 12/2001 |
| JP | 2002-509903 | 4/2002 |
| JP | 2002-539104 | 11/2002 |

(Continued)

*Primary Examiner*—Yvonne Eyler
*Assistant Examiner*—Jennifer Y Cho
(74) *Attorney, Agent, or Firm*—Wenderoth, Lind & Ponack, L.L.P.

(57) ABSTRACT

There is provided a process for producing (meth)acrylic acid including an absorption step of bringing a (meth)acrylic acid-containing gas obtained by a gas phase catalytic oxidation method into an absorption tower and allowing the gas to contact with an absorbent, in which absorption step a crude (meth)acrylic acid solution is withdrawn from a withdrawal outlet positioned between a supply point for the (meth)acrylic acid-containing gas and a supply point for the absorbent on the absorption tower, and then supplied to a next step. The process for producing (meth)acrylic acid makes it possible to suppress the formation of Michael adducts, thereby obtaining a (meth)acrylic acid containing solution in high yield and in high concentration.

5 Claims, 2 Drawing Sheets

FOREIGN PATENT DOCUMENTS

| | | |
|---|---|---|
| JP | 2003-171342 | 6/2003 |
| JP | 2004-51489 | 2/2004 |
| JP | 2004-359614 | 12/2004 |
| JP | 2004-359615 | 12/2004 |
| JP | 2005-511776 | 4/2005 |
| WO | 99/50220 | 10/1999 |

* cited by examiner

PROCESS FOR PRODUCING (METH) ACRYLIC ACID

BACKGROUND OF THE INVENTION

1. Field of the Invention

The present invention relates to a process for producing (meth)acrylic acid. The term "(meth)acrylic acid" as used herein means acrylic acid or methacrylic acid.

2. Description of the Related Art

In general, acrylic acid and methacrylic acid are useful raw materials widely used as the raw materials of chemical products, and various processes for their production have been proposed. For example, acrylic acid is produced by the gas phase catalytic oxidation of propylene and/or acrolein. Japanese Patent Laid-open Publications Nos. 2001-520213, 2004-359614, 2004-359615, and 2005-511776 disclose processes in which an acrylic acid-containing gas obtained by a gas phase catalytic oxidation method is absorbed into an absorbent to provide an acrylic acid containing solution, followed by distillation and/or crystallization steps, thereby obtaining purified acrylic acid. Japanese Patent Laid-open Publications Nos. 2001-516737, 2002-539104, and 2002-509903 disclose processes of directly obtaining crude acrylic acid from an acrylic acid-containing gas by fractional condensation.

These production processes have various improvements for the purpose of producing acrylic acid with high efficiency. In particular, regarding the method employing absorption with a solvent, there have been proposed, for the purpose of obtaining higher purity acrylic acid, a method of adding a polymerization inhibitor to be used in the separation and purification step (see Japanese Patent Laid-open Publication No. 2001-520213), a method of improving the rate of absorption of acrylic acid (see Japanese Patent Laid-open Publication No. 2004-359614), and a method of carrying out the purification of acrylic acid easily and simply by the use of a high concentration acrylic acid containing solution. In addition, Japanese Patent Laid-open Publication No. 2005-511776 proposes a method of forming acrylic acid with high efficiency in the gas phase catalytic oxidation reaction.

SUMMARY OF THE INVENTION

The above methods exhibit some degree of effects to improve the efficiency in the production of acrylic acid. However, in cases where absorption with a solvent is employed, there is room for further improvement. In particular, acrylic acid is an easily polymerizable substance, and Michael adducts are easily formed, such as acrylic acid dimer, trimer, and higher oligomers, by the reaction between acrylic acid molecules. As well as decreasing the yield of acrylic acid, these by-products increase the viscosity of an acrylic acid containing solution to become the cause of clogging in the pipes of a production apparatus, thereby decreasing the operability of the production apparatus.

The reaction of forming Michael adducts from acrylic acid is a reversible reaction, and therefore, a step of decomposing Michael adducts is provided as a part of the steps of the process for producing acrylic acid, and Michael adducts are recovered as acrylic acid. However, the employment of a new step requires additional equipment investment, resulting in an increase in the production cost of acrylic acid. In addition, even if a decomposition step is provided, it is difficult to completely decompose Michael adducts, and the loss of acrylic acid is difficult to be prevented.

Further, the by-products formed at the same time as the synthesis of (meth)acrylic acid may include substances having boiling points equal to or higher than that of (meth) acrylic acid, and as well as making complicated the separation and purification step, these high boiling point components are difficult to be completely removed.

The present invention has been completed, paying attention to the above circumstances, and it is an object of the present invention to provide a method of obtaining a (meth) acrylic acid containing solution having a small content of by-products as described above and having a high concentration of (meth)acrylic acid.

In view of the above problems, the present inventors have made a series of studies from the viewpoint of how to decrease the amounts of Michael adducts formed as by-products in the production of acrylic acid for the purpose of providing a process for producing (meth)acrylic acid with higher efficiency. As a result, they have been led to the production process of the present invention.

That is, a process for producing acrylic acid, which can attain the above object, comprises an absorption step of bringing a (meth)acrylic acid-containing gas obtained by a gas phase catalytic oxidation method into an absorption tower and allowing the gas to contact with an absorbent, thereby absorbing the (meth)acrylic acid as a crude (meth) acrylic acid solution, in which absorption step the crude (meth)acrylic acid solution is withdrawn above a supply point for the (meth)acrylic acid-containing gas and below a supply point for the absorbent on the absorption tower, and then supplied to a next step.

In cases where absorption with a solvent is usually carried out, (meth)acrylic acid absorbed into an absorbent in the absorption tower is collected as a (meth)acrylic acid solution at the bottom portion of the absorption tower, withdrawn as a bottom solution, and supplied to a next step. Therefore, at the bottom portion of the absorption tower, there are included, together with (meth)acrylic acid as an objective product, high boiling point components and by-products as described above, and these components are one of the causes to decrease the concentration of (meth)acrylic acid in the bottom solution withdrawn from the bottom portion of the absorption tower.

Thus, the present inventors have made a series of studies and found that if a crude (meth)acrylic acid solution formed in the absorption tower is withdrawn as a side flow of the absorption tower from a withdrawal outlet positioned between a supply point for the (meth)acrylic acid-containing gas and a supply point for the absorbent on the absorption tower, and then supplied to a next step, the formation amount of by-products such as Michael adducts can remarkably be decreased, thereby completing the production process of the present invention.

That is, the components having boiling points higher than that of (meth)acrylic acid, which are contained in the (meth) acrylic acid-containing gas, condensed or absorbed into an absorbent at a relatively low position of the absorption tower, and flows down toward the bottom portion of the absorption tower. On the other hand, (meth)acrylic acid in gas phase rises up in the absorption tower and is absorbed into an absorbent at a position higher than the position where high boiling point components are absorbed into an absorbent in the absorption tower. Therefore, the withdrawal of a (meth)acrylic acid solution as a side flow from the absorption tower makes it possible to obtain a (meth)acrylic acid solution having a small content of Michael adducts and high boiling point components and having a high concentration of (meth)acrylic acid.

In the above production process, the concentration of (meth)acrylic acid in the above (meth)acrylic acid solution withdrawn from the absorption tower may preferably be 80% mass or higher. In a preferred embodiment of the present invention, the next step to which the above crude (meth)acrylic acid solution is supplied is a step of separating and purifying (meth)acrylic acid from the crude (meth) acrylic acid solution obtained in the absorption step. The above separation and purification step may preferably include a crystallization step and/or a distillation step. As the above absorbent, it recommended to use water.

According to the production process of the present invention, a (meth)acrylic acid solution having a content of high boiling point components and solid matter suppressed to a low level, so that the step subsequent to the absorption step can be carried out with high efficiency. In addition, the formation amount of Michael adducts is decreased, so that (meth)acrylic acid formed in the reaction step can be recovered in higher yield. Therefore, if the production process of the present invention is employed, the step of treating by-products such as high boiling point components and Michael adducts can be simplified, for example, in the purification step.

DETAILED DESCRIPTION OF THE INVENTION

The process for producing (meth)acrylic acid according to the present invention comprises an absorption step of bringing a (meth)acrylic acid-containing gas obtained by a gas phase catalytic oxidation method into an absorption tower and allowing the gas to contact with an absorbent, thereby absorbing the (meth)acrylic acid as a crude (meth)acrylic acid solution, in which absorption step the crude (meth) acrylic acid solution is withdrawn from a withdrawal outlet positioned between a supply point for the (meth)acrylic acid-containing gas and a supply point for the absorbent, and then supplied to a next step.

The reason that a high concentration (meth)acrylic acid solution can be obtained by the production process of the present invention is as described above. The present inventors have further found that the production process of the present invention is also effective for decreasing a loss of (meth)acrylic acid to be caused by the formation of Michael adducts which are unavoidably formed in the production of (meth)acrylic acid.

That is, in the conventional method of withdrawing a (meth)acrylic acid solution from the bottom of an absorption tower, the Michael adducts are assumed to be mainly formed with their amounts being increased, while the (meth)acrylic acid solution is retained at the bottom of the absorption tower. Therefore, if the (meth)acrylic acid solution is withdrawn as a side flow of the absorption tower, the amount of (meth)acrylic acid withdrawn from the bottom of the absorption tower is decreased, so that the amounts of Michael adducts can be decreased.

In addition, if the crude (meth)acrylic acid solution is withdrawn as a side flow of the absorption tower, as in the production process of the present invention, the withdrawal amount of bottom solution per unit time is decreased, and the retention time of the bottom solution in the absorption tower becomes long. However, Michael adducts are formed by an equilibrium reaction, so that the formation rate of Michael adducts is high at the initial stage of the retention of the bottom solution, but is decreased with an increase in the amounts of Michael adducts. Therefore, even if the retention time of the bottom solution becomes long, the formation amounts of Michael adducts per unit time is decreased. It is assumed to be for this reason that the loss of (meth)acrylic acid can be reduced by employing the production process of the present invention.

The process for producing (meth)acrylic acid according to the present invention will be explained below.

[Synthesis of (meth)acrylic Acid]

First, the method of synthesizing (meth)acrylic acid according to the present invention will be explained.

As described above, the production process of the present invention is characterized in that a (meth)acrylic acid-containing gas formed in the reaction step is absorbed into an absorbent in an absorption tower, and a crude (meth) acrylic acid solution is withdrawn as a side flow of the absorption tower from a withdrawal outlet positioned between a supply point for the (meta)acrylic acid-containing gas and a supply point for the absorbent, and then supplied to a next step. Therefore, the other steps are not particularly limited, and any of the heretofore known methods can be employed. That is, the synthesis of (meth)acrylic acid may also be carried out by any of the heretofore known gas phase catalytic oxidation methods. For example, in cases where acrylic acid is synthesized, a starting material(s) for acrylic acid, such as propylene and/or acrolein, a molecular oxygen containing gas(es) such as air, and a dilution gas(es) are mixed with together to prepare a raw material gas. Then, the raw material gas is supplied to a reactor filled with a gas phase catalytic oxidation catalyst, and the gas phase catalytic oxidation reaction is carried out to give an acrylic acid-containing gas. In cases where methacrylic acid is synthesized, a raw material gas may be prepared from a starting material(s) such as isobutyrene and/or t-butyl alcohol in the same manner as in cases where acrylic acid is synthesized, and the gas phase catalytic oxidation reaction may be carried out.

The conditions at the time of the gas phase catalytic oxidation reaction are not particularly limited, and any of the heretofore known conditions may be employed. As the above raw material gas, a recycle gas formed in a (meth) acrylic acid absorption tower described below may be used. The reactor for carrying out the gas phase catalytic oxidation reaction is also not particularly limited, but the use of a multi-tube reactor is preferred from the viewpoint of its excellent reaction efficiency. In addition, the gas phase catalytic oxidation reaction may be carried out in a single reactor for two step reactions or in the tandem connection of two different reactors.

[Absorption Step]

Next, the absorption step according to the present invention will be explained. As described above, the absorption step is a step of bringing a (meth)acrylic acid-containing gas obtained by a gas phase catalytic oxidation method into an absorption tower and allowing the gas to contact with an absorbent, thereby absorbing the (meth)acrylic acid as a crude (meth)acrylic acid solution.

In the present invention, the (meth)acrylic acid-containing gas is introduced from the bottom portion of the absorption tower, whereas an absorbent into which the (meth)acrylic acid-containing gas is absorbed is introduced from the top portion of the absorption tower. The (meth)acrylic acid-containing gas introduced into the absorption tower is absorbed into the absorbent, while it rises up in the absorption tower, and a crude (meth)acrylic acid solution is formed. In the present invention, this crude (meth)acrylic acid solution is withdrawn as a side flow of the absorption tower from a withdrawal outlet positioned between a supply point for the (meth)acrylic acid-containing gas and a supply point for the absorbent, while it flows down toward the bottom portion of the absorption tower.

The Michael adducts, which have heretofore decreased the yield of (meth)acrylic acid and deteriorated the operability of the production of (meth)acrylic acid, and the solid matter such as polymers of (meth)acrylic acid, which has heretofore become the cause of the clogging and staining of pipes in the apparatus, are assumed to be mainly formed, while the (meth)acrylic acid solution is retained at the bottom portion of the absorption tower. Therefore, the formation amounts of by-products as described above can be decreased and it becomes possible to recover (meta)acrylic acid by employing the production process of the present invention, in which a crude (meth)acrylic acid solution is withdrawn as a side flow of the absorption tower.

In addition, high boiling point components contained in the (meth)acrylic acid-containing gas are introduced into the absorption tower, and then condensed or absorbed into an absorbent, prior to (meth)acrylic acid gas, so that the incorporation of the high boiling point components into the crude (meth)acrylic acid solution can be prevented by providing a withdrawal point for the crude (meth)acrylic acid solution above a supply point for the (meth)acrylic acid-containing gas.

The term "high boiling point components" as used herein means components having boiling points higher than that of (meth)acrylic acid under the standard conditions. The term "low boiling point components" as used herein means components having boiling points lower than (meth)acrylic acid under the standard conditions.

The absorption tower which can be used in the present invention is not particularly limited, so long as a (meth) acrylic acid-containing gas and an absorbent for absorbing (meth)acrylic acid can sufficiently be brought into contact with each other. For example, any of the heretofore known absorption towers, such as tray towers, packed towers, wetted wall towers, and spray towers, can be used.

The method for bringing the (meth)acrylic acid-containing gas and the absorbent into contact with each other in the absorption tower is not particularly limited. For example, any of the heretofore known contact methods can be used, such as cross flow contact using bubble-cap trays, uniflat trays, perforated trays, jet trays, bubble trays, or Venturi trays; or counter flow contact using turbogrid trays, dual float trays, ripple trays, kittel trays, gauze-type, sheet-type, or grid-type regular fillers, or irregular fillers.

The supply point for the absorbent may preferably be provided at the top of the absorption tower in order to carry out the contact with the (meth)acrylic acid-containing gas with high efficiency. If there is no problem with the absorption of the (meth)acrylic acid-containing gas, the supply point for the absorbent may preferably be provided within the range of from 1% to 30%, more preferably from 1% to 20%, and still more preferably from 1% to 10%, of the total theoretical plate number, counted from the top portion to the bottom portion of the absorption tower, with the base point being on the top side of the absorption tower.

On the other hand, the supply point for the (meth)acrylic acid-containing gas may preferably be provided within the range of from 50% to 100% (i.e., on the bottom side from the middle portion in the height direction of the absorption tower; e.g., at the position within the range of from the 50th plate to the 100th plate in cases where the top of the absorption tower is referred to as the 1st plate and the bottom of the absorption tower is referred to as the 100th plate), more preferably from 70% to 100%, and still more preferably from 90% to 100%, of the total theoretical plate number, counted from the top portion to the bottom portion of the absorption tower, with the base point being on the top side of the absorption tower.

Figure 1:
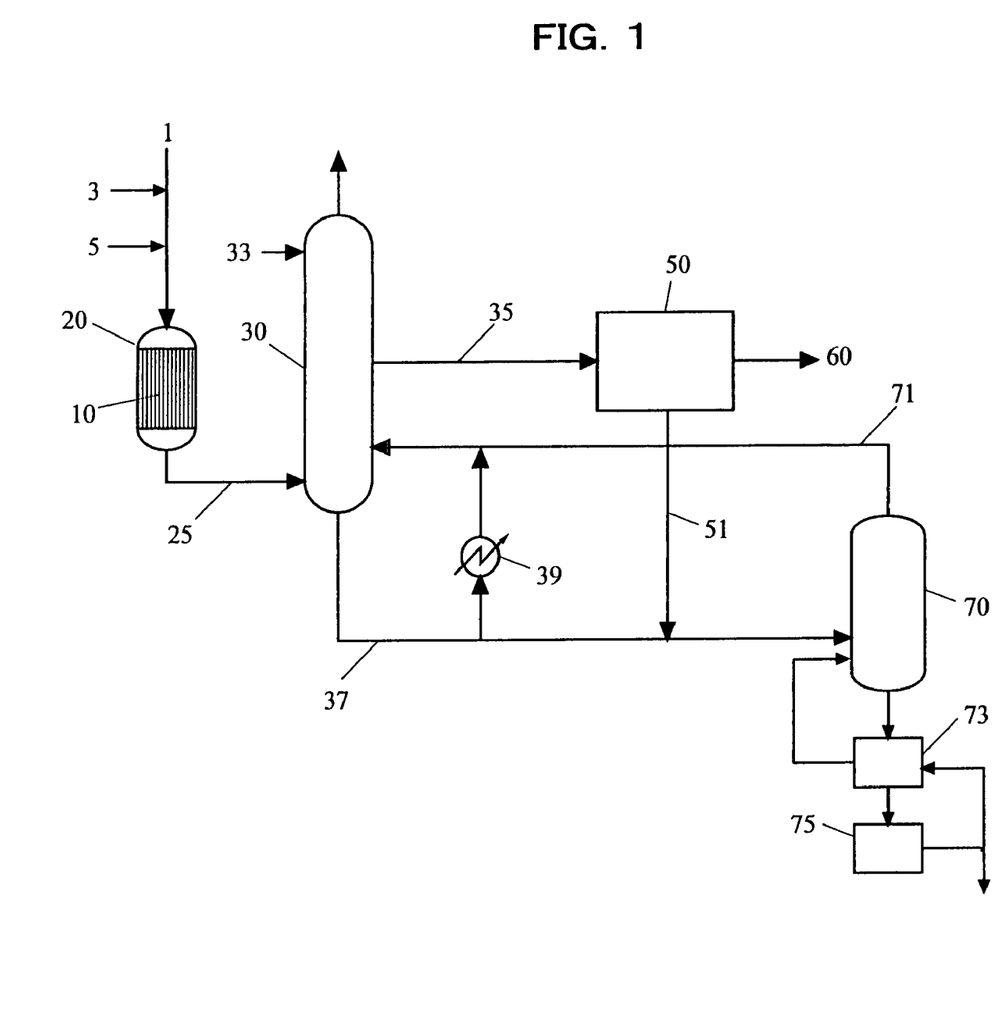
FIG. 1 is a process drawing showing a preferred embodiment of the present invention.

The withdrawal outlet for the crude (meth)acrylic acid solution may be positioned between the supply point for the (meth)acrylic acid-containing gas and the introduction inlet for the absorbent. From the viewpoint that the purification step is carried out with high efficiency, the withdrawal outlet for the crude (meth)acrylic acid solution 35 may preferably be provided on the top side compared with the supply position for the (meth)acrylic acid-containing gas 25, as illustrated in FIG. 1 showing a typical example of the production process of the present invention. On the other hand, if the position of the withdrawal outlet is too high, the crude (meth)acrylic acid solution may have a decreased concentration of (meth)acrylic acid, and the amount of (meth)acrylic acid discharged from the top of the absorption tower may be increased (i.e., an increase in the loss rate of (meth)acrylic acid). The gas discharged from the top of the absorption tower is usually used as a recycle gas at the time of the synthesis of (meth)acrylic acid, or after cooled, the condensable substances contained in the gas are used as part of the absorbent in the absorption tower. However, in cases where the loss rate of (meth)acrylic acid is high, the loads in the absorption tower, in the reactor, and in the cooling step become great, which is disadvantage from the viewpoints of equipment investment and utility. Therefore, the withdrawal outlet for the crude (meth)acrylic acid solution may preferably be provided within the range of from 20% to 99%, more preferably from 50% to 99%, still more preferably from 70% to 99%, and most preferably 80% to 99%, of the total theoretical plate number with the base point being at the top side of the absorption tower. If the withdrawal outlet for the crude (meth)acrylic acid solution is provided within the above range in the absorption tower, the crude (meth)acrylic acid solution can have a small content of Michael adducts and polymers of (meth)acrylic acid and can also have a high concentration of (meth)acrylic acid. In addition, the content of high boiling point components formed as by-products at the time of the gas phase catalytic oxidation reaction (e.g., maleic acid, benzaldehyde, furfural, protoanemonin) can be suppressed to a low level. Further, also for the purpose of decreasing the loss rate of (meth)acrylic acid, the withdrawal outlet for the crude (meth)acrylic acid solution may preferably be provided within the above range.

For the purpose of withdrawing the crude (meth)acrylic acid solution with high efficiency, the withdrawal outlet for the crude (meth)acrylic acid solution may preferably be provided with a liquid collector.

The amount of the crude (meth)acrylic acid solution withdrawn as a side flow of the absorption tower may preferably be set in the range of from not smaller than 20% by mass, more preferably not smaller than 50% by mass, still more preferably not smaller than 75% by mass, and not greater than 96.0% by mass, relative to the amount of the solution withdrawn from the absorption tower (i.e. the total amount of the side flow and the bottom solution) In order to decrease the formation amounts of Michael adducts, the withdrawal amount may preferably be as high as possible. However, in cases where the withdrawal amount is too high, the high boiling point components and solid matter hardly dissolved in the absorbent may be accumulated at the bottom of the absorption tower, so that the bottom solution may have a high viscosity or the pipes in the apparatus may be clogged, thereby making it difficult to continue the operation of the absorption tower.

The concentration of (meth)acrylic acid in the crude (meth)acrylic acid solution withdrawn from the absorption tower may preferably be 80% by mass or higher, more preferably 85% by mass or higher, and still more preferably 90% by mass or higher.

The absorbent is not particularly limited, so long as it can absorb and dissolve (meth)acrylic acid, but any of the heretofore known absorbents can be used, such as diphenyl ether, diphenyl, mixtures of diphenyl ether and diphenyl, water, organic acid containing water generated from the (meth)acrylic acid purification step (e.g., condensed liquid obtained by cooling gas discharged from the top of the absorption tower (i.e., recycle gas) to condense condensable substances contained in the gas). In these absorbents, water and/or organic acid containing water generated from the (meth)acrylic acid purification step may preferably be used.

Of the gas discharged from the top of the absorption tower, the discharged gas to be recycled to the reactor (i.e., the synthesis of (meth)acrylic acid) is referred to herein as "recycle gas" and the gas to be discharged from the top of the absorption tower to the outside of the system is referred to herein as "waste gas".

The method of cooling the recycle gas is not particularly limited, but it may use an apparatus which can condense condensable substances contained in the recycle gas. For example, there can be used any of the heretofore known heat exchangers such as multi-tube type heat exchangers, fin-tube type heat exchangers, air-cooled type heat exchangers, double-tube type heat exchangers, coil type heat exchangers, direct-contact type heat exchangers, and plate type heat exchangers. The condensed liquid generated by cooling of the recycle gas may often contain polymerizable substances such as (meth)acrylic acid. Therefore, for example, if the cooling method using a cooling tower in combination with a cooler is employed, the supply of a polymerization inhibitor(s) becomes easy, which is preferred.

The cooling temperature of the recycle gas is not particularly limited. The concentration of water in the total raw material gas supplied to the reactor may preferably be set to be in the range of from 0% to 10% by volume, more preferably from 0% to 7% by volume, and particularly preferably from 0% to 6% by volume. Further, it is recommended that the total concentration of acids in the total raw material gas supplied to the reactor should preferably be set in the range of from 0% to 0.2% by volume, and more preferably from 0% to 0.1% by volume. Therefore, the cooling may preferably be carried out to condense condensable substances so that the amount of water contained both in the recycle gas and in the raw material gas can fall within the above range. In cases where air is used as the molecular oxygen containing gas, water is contained in the air. In such cases, the amount of water after cooling of the recycle gas is determined both from the preferred concentration of water contained in the raw material gas and from the amounts of raw material gas and air to be mixed, and the cooling may be carried out so that the preferred concentration of water can be attained. As an index of the cooling temperature, the cooling may preferably be carried out so that the temperature of the recycle gas can become lower than the temperature of the waste gas by from 1° C. to 50° C., more preferably from 2° C. to 40° C., and particularly from 3° C. to 30° C.

The term "condensable substances" as used herein means substances which are in liquid state at 20° C. under the standard atmospheric pressure.

The mass of the absorbent supplied to the absorption tower may appropriately be determined by the concentration of the objective crude (meth)acrylic acid solution. In order to carry out the purification of (meth)acrylic acid with high efficiency, the concentration of (meth)acrylic acid may preferably be as high as possible. From such a viewpoint, it is recommended that the mass flow rate of the absorbent introduced into the absorption tower should preferably be set to be not less than 0.1 times, more preferably not less than 0.15 times, and should preferably be set to be not more than 1.5 times, more preferably not more than 1.0 times, and still more preferably not more than 0.8 times, the mass flow rate of (meth)acrylic acid contained in the (meth)acrylic acid-containing gas. In cases where the mass flow ratio of the absorbent is too low, it may cause an extreme decrease in the efficiency of the absorption for (meth)acrylic acid. On the other hand, in cases where the mass flow ratio of the absorbent is too high, it may becomes difficult to obtain a high concentration (meth)acrylic acid solution.

The temperature of the absorbent introduced into the absorption tower may preferably be set to be in the range of from 0° C. to 60° C., more preferably from 10° C. to 50° C. In order to make the absorbent have a preferred temperature, there may be used, if necessary, any of the heretofore known heat exchangers such as multi-tube type heat exchangers, double-tube type heat exchangers, spiral type heat exchangers, and plate type heat exchangers.

For the purpose of preventing the polymerization of polymerizable substances in the absorption tower, any of the heretofore known polymerization inhibitors may be added to the absorbent. The polymerization inhibitors may include one or more kinds of compounds selected from the group consisting of N-oxyl compounds, phenol compounds, manganese salts such as manganese acetate, dialkyldithiocarbamic acid copper salts such as copper dibutylthiocarbamate, nitroso compounds, amine compounds, and phenothiazine, as described, for example, in Japanese Patent Laid-open Publications Nos. 2001-348360, 2001-348358, and 2001-348359.

It is recommended that the absorption tower for (meth) acrylic acid should preferably be operated under a pressure (gauge pressure) of from 0 to 0.4 MPa, more preferably of 0.1 MPa or lower, and still more preferably of 0.03 MPa or lower, at the top of the absorption tower. In cases where the pressure at the top of the absorption tower is too low, it may require a pressure reducing apparatus, resulting in high equipment cost and high utilities cost. On the other hand, the pressure at the top of the absorption tower is too high, it may become necessary to increase the temperature of the absorption tower for the purpose of discharging low boiling point substances from the top of the absorption tower, resulting in a decrease in the absorption efficiency for (meth)acrylic acid. It is recommended that the temperature at the top of the absorption tower should preferably be set to be 30° C. or higher, more preferably 40° C. or higher, and should preferably be set to be 85° C. or lower, more preferably 80° C. or lower.

The bottom solution residing at the bottom portion of the absorption tower in the absorption step is rich in the content of high boiling point components, and may therefore be discarded. However, there are some cases where it contains (meth)acrylic acid and Michael adducts, and therefore, part of the bottom solution may be supplied to a step of carrying out distillation, the decomposition of Michael adducts, or the like, for the purpose of improving the yield of (meth)acrylic acid. In addition, part of the bottom solution may be cooled or heated and then returned to the absorption tower.

On the other hand, the crude (meth)acrylic acid solution withdrawn as a side flow of the absorption tower in the absorption step is supplied to a next step. For example, the crude (meth)acrylic acid solution may be supplied to the esterification reaction step as a starting material of (meth) acrylic acid esters without being further treated, or may be supplied to the separation and purification step in order to prepare high purity (meth)acrylic acid.

The production process of the present invention is characterized by the above-described absorption step for (meth) acrylic acid. The other steps than the absorption step are not particularly limited, but they can be carried out by any of the heretofore known methods or by addition of appropriate changes or modifications to any of the heretofore known methods.

[Next Step Example 1: Esterification Step]

First, as the next step, cases where esterification is carried out will be explained. The method of esterification is not particularly limited, and any of the heretofore known methods can be employed. For example, there can be mentioned methods in which the crude (meth)acrylic acid solution obtained in the absorption step and an alcohol(s) are allowed to cause esterification under the presence of an acid catalyst(s) methods in which the crude (meth)acrylic acid solution obtained in the absorption step and an alkylene oxide(s) are allowed to cause esterification under the presence of a catalyst(s), and some other methods.

Examples of the alcohol may include saturated or unsaturated aliphatic alcohols having 1 to 12 carbon atoms, alicyclic alcohols having 3 to 10 carbon atoms, and aromatic alcohols having 6 to 10 carbon atoms. In these alcohols, preferred are aliphatic alcohols having 1 to 12 carbon atoms and alicyclic alcohols having 3 to 10 carbon atoms, of which typical examples may include methanol, ethanol, n-propanol, isopropanol, n-butanol, isobutanol, sec-butanol, tert-butanol, 1-pentanol, 2-pentanol, 3-pentanol, cyclopentanol, 1-hexanol, 2-hexanol, 3-hexanol, cyclohexanol, 1-heptanol, 2-heptanol, 3-heptanol, 1-octanol, isooctanol, 2-ethylhexanol, isononyl alcohol, and lauryl alcohol. These alcohols may be used alone, and two or more kinds of them may also be used in combination.

Examples of the alkylene oxide may include alkylene oxides having 2 to 6 carbon atoms, of which typical examples may include ethylene oxide, propylene oxide, and butylenes oxide. These alkylene oxides may be used alone, or two or more kinds of them may also be used in combination.

Examples of the acid catalyst may include cation exchange resins. The cation exchange resins are not particularly limited to any of the resin structures or physical properties such as degree of cross-linking, but it is preferred to use strong acid cation exchange resins of the porous or gel type. Typical examples of the strong acid cation exchange resins of the porous type may include MSC-1 (available from Dow Chemical Company); PK-208, PK-212, PK-216, PK-220, PK-228 (all available from Mitsubishi Chemical Corporation); AMBERLYST-16 (wherein "AMBERLYST" is a registered trade mark own by Rohm and Haas Company), IR-116, IR-118, IR-122, C-26, C-26TR, C-264, C-265 (all available from Rohm and Haas Company); SPC-108, SPC-112 (both available from Bayer AG); and KC-470 (available from Sumitomo Chemical Co., Ltd.). Typical examples of the strong acid cation exchange resins of the gel type may include HCR-S, HCR-W2, HGR-W2 (all available from Dow Chemical Company); SK-1B, SK-106, SK-110 (all available from Mitsubishi Chemical Corporation); DUOLITE C20H, C255LFH (both available from Roam and Haas Company; "DUOLITE" is a registered trade mark own by Roam and Haas Company); and K1221, K1431 (both available from Bayer AG). Of course, the acid catalyst is not particularly limited to these strong acid cation exchange resins, but weak acid cation exchange resins or inorganic acids such as sulfuric acid may be used. These cation exchange resins and inorganic acids may be used alone, or two or more kinds of them may also be used in combination. When the crude (meth)acrylic acid solution and an alkylene oxide(s) are allowed to cause esterification, a metal catalyst(s) containing chromium, iron, and the like can be used. The specific method and various conditions, such as reaction temperature, employed in the esterification step may appropriately be set, and are not particularly limited.

The esterification step is followed by the separation and purification step including distillation, emission, crystallization, extraction, partial condensation, filtration, or an appropriate combination thereof, resulting in obtaining a (meth) acrylic acid alkyl ester(s) or a (meth)acrylic acid hydroxyalkyl ester(s), which is a product(s).

[Next Step Example 2: Purification Step]

Next, cases where purification is carried out in a next step subsequent to the absorption step will be explained. As the method of purifying (meth)acrylic acid, there can be employed any of the methods including distillation, emission, crystallization, extraction, partial condensation, or an appropriate combination thereof. In cases where water is used as an absorbent in the absorption step, the purification step may include an azeotropic distillation dehydration step in part of the distillation step. In cases where the crude (meth)acrylic acid solution supplied to the purification step is a high concentration (meth)acrylic acid solution having a (meth)acrylic acid concentration of 70% by mass or higher, preferably 80% by mass or higher, and more preferably 85% by mass or higher, the purification of (meth)acrylic acid may preferably be carried out by any of the crystallization methods.

For example, in cases where purification by crystallization is carried out, there is no limitation in the crystallization methods which can be used. The crystallization methods may be any of the continuous type and the batch type, and the operation of crystallization may be carried out at one stage or at two or more stages.

As the crystallizer of the continuous type, there can be used, for example, Backmixing Column Crystallizer (BMC; available from Nippon Steel Chemical Co., Ltd.) in which a crystallization portion, a solid-liquid separation portion, and a crystal purification portion are combined as one unit of the tower type; or any of the crystallizers including a combination of a crystallization portion (e.g., Cooling Disk Crystallizer (CDC; available from GMF-Gouda)), a solid-liquid separation portion (e.g., a belt filter, a centrifugal separator), and a crystal purification portion (e.g., Kureha Crystal Purifier (KCP; available from Kureha Techno Eng Co., Ltd.)).

As the crystallizer of the batch type, there can be used, for example, a layer crystallizer available from Sulzer Chemtech Ltd. (i.e., dynamic crystallizer), a static crystallizer available from BEFS PROKEM, or the like.

The conditions for operating the above crystallizers and the number of crystallization may appropriately be determined depending upon the concentration of the crude (meth)acrylic acid solution supplied to the crystallizer and the purity of the objective purified (meth)acrylic acid.

In ceases where purification by distillation is carried out, various embodiments can be employed: for example, in one embodiment, low boiling point components contained in the crude (meth)acrylic acid solution are removed from the top portion of a distillation tower, high boiling point components contained in the crude (meth)acrylic acid solution are removed from the bottom portion of the distillation tower, and (meth)acrylic acid, which is a product, is obtained from the middle portion of the distillation tower; or in another embodiment, distillation towers are separately provided for the purpose of removing each of low boiling point components and high boiling point components, thereby obtaining purified (meth)acrylic acid. Examples of the distillation towers which can be used in such purification methods may include tray towers having two or more trays therein and packed towers filled with packings. The trays provided in the tray towers and the packings filled in the packed towers can be the same as those in the absorption tower used in the absorption step. The (meth)acrylic acid purified by the distillation tower(s) may be used as a product without being further treated, or may further be purified by any of the crystallization methods.

The distillation tower may be provided, if necessary, with a reboiler for controlling the temperature in the tower, a condenser for cooling or refluxing steam flowing out from the top of the tower, a vacuum apparatus, and the like.

The conditions for operating the distillation tower are not particularly limited, but may appropriately be determined depending upon the concentration of the crude (meth)acrylic acid solution supplied to the tower and the purity of the objective purified (meth)acrylic acid. For example, it is recommended that the pressure (absolute pressure) at the top of the distillation tower should preferably be set to be in the range of from 20 to 400 hPa, more preferably from 30 to 300 hPa, and still more preferably from 30 to 200 hPa; the temperature at the top of the distillation tower should preferably be set to be in the range of from 30° C. to 70° C., more preferably from 40° C. to 60° C.; and the temperature at the bottom of the distillation tower should preferably be set to be in the range of 70° C. to 120° C., more preferably from 80° C. to 110° C.

In the purification step, the remaining mother liquid discharged as a residue (in cases of the distillation methods) or the bottom solution(s) of the distillation tower(s) (in cases of the distillation methods) may be discharged as a waste liquid to the outside of the system, but may be supplied to the step of recovering the useful components contained in the residue. The recovery step is not particularly limited, but may include the distillation step of recovering (meth)acrylic acid remaining in the residue, and the step of decomposing Michael adducts and recovering them as (meth)acrylic acid.

As described above, the production process of the present invention can hardly involve the formation of Michael adducts. Therefore, the decomposition step can be made to be in a small scale and simple form as compared with that in the conventional methods.

The decomposition step is not particularly limited, so long as it can decompose Michael adducts and recover them as (meth)acrylic acid, but any of the heretofore known methods and apparatuses can be employed. For example, as the apparatus which can be employed in the decomposition step, there can be mentioned thin-film evaporators provided with thermal decomposition baths, and distillers which can distill, at the same time as the decomposition of Michael adducts, the decomposed products. The (meth)acrylic acid obtained in the decomposition step or in the distillation step may be supplied to the absorption tower (i.e., the absorption step) or the purification step.

Referring to FIG. 1, a typical example of the process for producing (meth)acrylic acid according to the present invention will be explained. The production process of the present invention is not limited to this typical example, but can be carried out by addition of appropriate changes or modifications without inhibiting the advantageous effects of the present invention.

First, a raw material gas obtained by mixing (meth)acrylic acid starting material 1 such as propylene and/or acrolein, molecular oxygen containing gas 3 such as air, and dilution gas 5, is supplied to reactor 20 filled with gas phase catalytic oxidation catalyst 10, thereby obtaining (meth)acrylic acid-containing gas 25 by gas phase catalytic oxidation reaction. The (meth)acrylic acid-containing gas 25 obtained is supplied to the bottom of absorption tower 30, in which this gas 25 is brought into contact with absorbent 33 supplied from the top of the absorption tower 30, thereby obtaining a crude (meth)acrylic acid solution. In FIG. 1, distillate liquid 71 from distillation tower 70 (this is referred to as a tower for the separation of high boiling point components) as described below is supplied to the absorption tower 30. However, the production process of the present invention is, of course, not particularly limited to such an embodiment, but part of the distillate liquid 71 may be discharged to the outside of the system. In addition, the discharged gas from the top of the absorption tower 30 may be recycled as a recycle gas to the reactor 20. At that time, after separating condensable components contained in the discharged gas by cooling, the condensable components (in the form of a condensed liquid) may be mixed with absorbent 33, and this mixture may be supplied to the absorption tower 30 (not shown in FIG. 1).

Then, crude (meth)acrylic acid solution 35 is withdrawn above the supply point for the (meth)acrylic acid-containing gas 25 on the absorption tower 30 and below the supply point for the absorbent 33 on the absorption tower 30. The crude (meth)acrylic acid solution 35 obtained is supplied to crystallizer 50, followed by purification, thereby obtaining product (meth)acrylic acid 60.

On the other hand, the residual mother liquid from the crystallizer 50 may be discharged in full to the outside of the system (not shown in FIG. 1). The residual mother liquid from the crystallizer 50 may also be supplied in part or full as crystallization residual mother liquid 51, together with the bottom liquid 37 discharged from the absorption tower 30, to the distillation tower 70. Of course, the bottom liquid 37 may be supplied in full to the distillation tower 70 (referred to in this case as a tower for separating high boiling point components), or may be discharged in part of full to the outside of the system (not shown in FIG. 1), or may be cooled in part with heat exchanger 39 and then recycled to the absorption tower 30. In addition, the crystallization residual mother liquid 51 from the crystallizer 50 may be mixed with the distillate liquid 71 from the distillation tower 70 and then supplied to the absorption tower 30. It is recommended that the crystallization residual mother liquid 51 should preferably be mixed with the bottom liquid 37 of the absorption tower 30 and then supplied to the distillation tower 70 for separating high boiling point components.

In the distillation tower 70, low boiling point components and (meth)acrylic acid contained in the bottom liquid 37 of the absorption tower 30 and the crystallization residual mother liquid 51 are distilled from the top thereof, and the distillate liquid 71 is recycled to the absorption tower 30. On the other hand, high boiling point components contained in the bottom liquid of the distillation tower 70 include Michael adducts. These Michael adducts are supplied through thin film evaporator 73 to thermal decomposition bath 75 and then allowed to reside therein to thermally decompose into (meth)acrylic acid (i.e., a Michael adducts decomposition step). The (meth)acrylic acid formed by thermal decomposition is returned to the thin film evaporator 73, so that it is distillated from the top of the distillation tower 70 to become the distillate liquid 71, which is then recycled to the absorption tower 30, thereby finally recovering it as the product (meth)acrylic acid 60.

Figure 2:
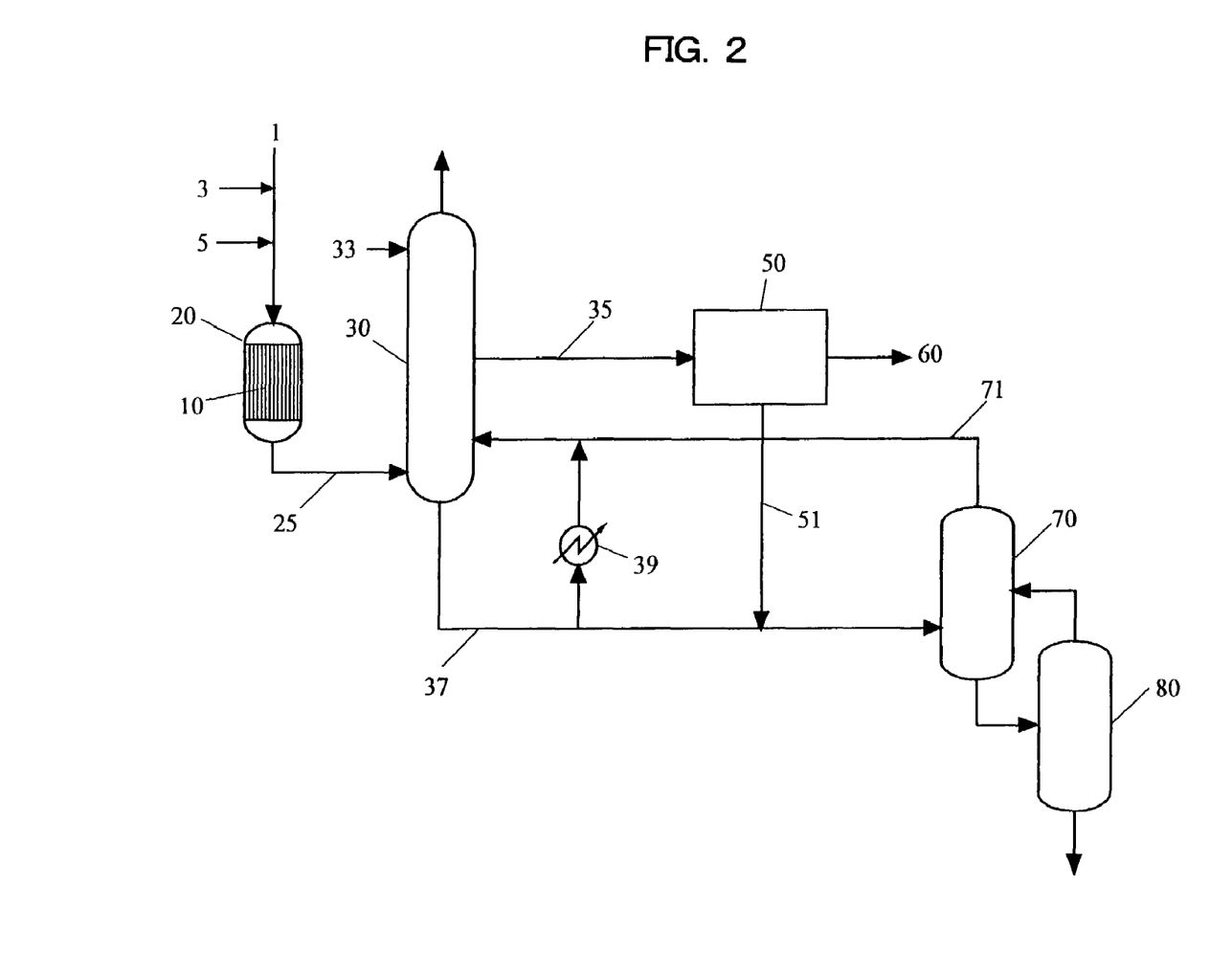
FIG. 2 is a process drawing showing another preferred embodiment of the present invention.

In the Michael adducts decomposition step, any of the reactive distillation systems may be employed, such as those in which the decomposition of Michael adducts and the distillation of (meth)acrylic acid formed occur at the same time, so that the decomposition reaction of Michael adducts is promoted and the equilibrium is shifted toward the direction of increasing the formation amount of (meth) acrylic acid. For example, as shown in FIG. 2, the bottom liquid of the distillation tower 70 is supplied to reactive distillation apparatus 80 in which the decomposition of Michael adducts and the distillation of (meth)acrylic acid formed are carried out at the same time. The top liquid containing (meth)acrylic acid is recycled to the distillation tower 70, whereas the bottom liquid containing high boiling point components is discharged as a waste oil to the outside of the system.

In FIGS. 1 and 2, there is shown an example employing the crystallization method as the purification step. However, any of the purification steps other than the crystallization method may be employed, and as a step prior to the purification step, any of the esterification steps may be provided.

As described above, the production process of the present invention is characterized in that the crude (meth)acrylic acid solution is withdrawn as a side flow of the absorption tower. Therefore, high boiling point components (i.e., components having boiling points higher than (meth)acrylic acid) containing Michael adducts are easily accumulated at the bottom portion of the absorption tower. Michael adducts can be recovered as (meth)acrylic acid by decomposition, and therefore, the production process of the present invention may be provided with a step of carrying out the decomposition of the bottom liquid of the absorption tower (i.e., a decomposition step). The decomposition step is not limited to the method as described above, but even any of the steps of producing (meth)acrylic acid using the other methods can be employed. For example, in cases where high boiling point components are concentrated at the bottom portion of the absorption tower, depending upon the conditions of producing (meth)acrylic acid and the conditions of operating the absorption tower, the bottom liquid of the absorption tower may preferably be withdrawn and then decomposed in the Michael adducts decomposition step.

The step of decomposing Michael adducts or treating high boiling point components is usually provided near the final stage of the purification step and may be a step of decomposing a waste oil discharged from a tower for separating high boiling point components (e.g., see Japanese Patent Laid-open Publication No. 11-12222) or a step of decomposing high boiling point components after separating acrylic acid and high boiling point components from the bottom liquid discharged from an azeotropic dehydration tower (e.g., see Japanese Patent Laid-open Publication No. 2004-51489). In contrast, the above step is a step of decomposing Michael adducts contained in the bottom liquid of the absorption tower without being supplied to the purification step or any other step, and particularly in cases where high boiling point components are easily accumulated at the bottom portion of the absorption tower, (meth)acrylic acid can be produced with higher efficiency by employing the above step.

The bottom liquid of the absorption tower, i.e., a bottom liquid accumulated at the bottom portion of the absorption tower in cases where the crude (meth)acrylic acid solution is withdrawn as a side flow of the absorption tower, may be supplied to the decomposition step by way of the distillation step (i.e., a step for separating high boiling point components). The bottom liquid of the absorption tower, which was supplied to the decomposition step, may be recycled to the absorption tower, either directly or by way of the tower for separating high boiling point components. This makes it possible that (meth)acrylic acid purified by decomposition of the bottom liquid of the absorption tower is absorbed, together with (meth)acrylic acid derived from the reaction step, into the absorbent and then withdrawn as the crude (meth)acrylic acid solution from the absorption tower.

The step of decomposing the bottom liquid of the absorption tower (i.e., the decomposing treatment of Michael adducts) may be carried out either at a step provided with a tower for separating high boiling point components in addition to a thin film evaporator and a thermal decomposition tank (e.g., see FIG. 1), as disclosed in Japanese Patent Laid-open Publication No. 11-12222, or at a step employing the reactive distillation system in which the decomposition of Michael adducts and the distillation of (meth)acrylic acid after the decomposition are carried out at the same time (e.g., see FIG. 2), as disclosed in Japanese Patent Laid-open Publication No. 2003-171342. In these steps, the step employing the reactive distillation system is preferred to the step provided with a tower for separating high boiling point components in addition to a thin film evaporator and a thermal decomposition tank because acrylic acid can be recovered with high efficiency from the bottom solution of the absorption tower. Further, in either case, a polymerization inhibitor(s) may be used, if necessary.

EXAMPLES

The present invention will be described below in detail by reference to Examples and Comparative Examples, but the present invention is not limited to these Examples. The present invention can be put into practice after appropriate modifications or variations within a range meeting the gists described above and later, all of which are included in the technical scope of the present invention.

Experimental Examples 1 and 2

Absorption of Acrylic Acid

According to the following method, the absorption of acrylic acid was carried out. In Experimental Example 1, the position of withdrawing a crude acrylic acid solution was fixed at the specific position (i.e., the position corresponding to 89% of the total theoretical plate number, counted from the top portion to the bottom portion of an absorption tower, with the base point being on the top side of the absorption tower), and the amount of the crude acrylic acid solution was changed. In Experimental Example 2, the position of withdrawing a crude acrylic acid solution was changed, and the amount of the crude acrylic acid solution was fixed at the specific amount (i.e., at the withdrawal amount of 6 kg).

Experimental Example 1

As the absorption tower, there was used a tower having a gas outlet at the top thereof and a bottom liquid outlet at the bottom thereof and being charged with packings so that it has the calculated total theoretical plate number of 18. In the absorption tower, an acrylic acid-containing gas inlet was provided below the lowest position of the packings, and an absorbent introduction inlet and a liquid distributor for distributing the absorbent in the absorption tower were provided above the highest position of the packings. Further, in the absorption tower, a liquid collector is provided at the position corresponding to 89% of the total theoretical plate number, counted from the top portion to the bottom portion of the absorption tower, with the base point being on the top side of the absorption tower (i.e., at the position corresponding to the theoretical plate number thereof being 16, counted from the highest plate of packings), from which position the crude acrylic acid solution was withdrawn.

The temperature and pressure at the top of the absorption tower was controlled to 69.6° C. and 0.015 MPa, respectively, at which the absorption of acrylic acid was carried out. The temperature control of the absorption tower was carried out by cooling and recycling part of the bottom liquid.

The acrylic acid-containing gas (composition: 7.1% byvolume of acrylicacid, 13.9% byvolume ofwater, 74.2% byvolume of nitrogen gas, 1.5% byvolume of oxygen gas, 3.3% by volume of others (e.g., propylene, propane, $CO_x$, acetic acid, aldehydes)) obtained by a gas phase catalytic oxidation method was introduced at a temperature of 270° C. at a flow rate of 34.9 $Nm^3$/hour from the acrylic acid-containing gas inlet (at the position corresponding to 100% of the total theoretical plate number, counted from the top portion to the bottom portion of the absorption tower, with the base point being on the top side of the absorption tower; or the theoretical plate number thereof being 18) into the absorption tower, at which same time the absorbent (i.e., water:acrylic acid:acetic acid:others=95:2:2:1, containing 4-hydroxy-2,2,6,6-tetra-methylpyperidinoxyl (TEMPO) at an amount corresponding to 200 ppm by mass, relative to acrylic acid in the acrylic acid-containing gas) was introduced at a flow rate of 4.5 kg/hour from the absorbent inlet into the absorption tower. In the absorption tower, the acrylic acid-containing gas was brought into contact with the absorbent, so that the acrylic acid-containing gas was absorbed into the absorbent, resulting in the crude acrylic acid solution, which was withdrawn from the absorption tower by way of the liquid collector provided on the bottom portion side from the middle of the absorption tower (i.e., at the position corresponding to 89% of the total theoretical plate number, counted from the top portion to the bottom portion of the absorption tower, with the base point being on the top side of the absorption tower).

The composition and withdrawal amount of the crude acrylic acid solution obtained are shown in Table 1, together with the composition of the bottom liquid of the absorption tower. In Table 1, the term "side flow" means the crude acrylic acid solution withdrawn on the bottom portion side from the middle of the absorption tower (i.e., at the position corresponding to 89% of the total theoretical plate number, counted from the top portion to the bottom portion of the absorption tower, with the base point being on the top side of the absorption tower; or the theoretical plate number thereof being 16); the term "bottom liquid" means the liquid withdrawn from the bottom portion of the absorption tower; and the term "dimer" means the Michael adduct formed by the reaction of two acrylic acid molecules (i.e., acrylic acid dimer). In addition, the term "ratio of side flow withdrawal amount" means the ratio of the mass of the side flow (i.e., the crude acrylic acid solution) to the total mass of the side flow and the bottom liquid. Further, the term "top loss rate" means the ratio of the amount of the acrylic acid-containing gas discharged from the absorption tower without being absorbed into the absorbent to the amount of the acrylic acid-containing gas introduced into the absorption tower.

In Experimental Examples 1-1 to 1-6, the crude acrylic acid solution was withdrawn from the side portion of the absorption tower. In Experimental Example 1-7, the crude acrylic acid solution was withdrawn as the bottom liquid of the absorption tower. In Experimental Examples 1-1 to 1-6, the absorption of acrylic acid was carried out under the same conditions, except for the withdrawal amount of the crude acrylic acid solution.

TABLE 1

| | | Experimental Example | | | | | | |
|---|---|---|---|---|---|---|---|---|
| | | 1-1 | 1-2 | 1-3 | 1-4 | 1-5 | 1-6 | 1-7 |
| Side flow | Mass (kg/hour) | 2.0 | 4.0 | 6.0 | 6.5 | 7.0 | 7.5 | 0.0 |
| | Acrylic acid concentration (%) | 92.35 | 92.56 | 92.75 | 92.8 | 92.84 | 92.89 | 92.40* |
| | Dimer concentration (%) | 0 | 0 | 0 | 0 | 0 | 0 | 1.65* |
| | Solid matter concentration (ppm) | 0 | 0 | 0 | 0 | 0 | 0 | — |
| Bottom liquid | Mass (kg/hour) | 6.21 | 4.23 | 2.25 | 1.75 | 1.25 | 0.76 | 8.19 |
| | Dimer mass (kg/hour) | 0.117 | 0.099 | 0.075 | 0.067 | 0.058 | 0.047 | 0.135 |
| | Solid matter concentration (ppm) | 7 | 10 | 18 | 24 | 33 | 54 | 5 |

TABLE 1-continued

| | Experimental Example | | | | | | |
|---|---|---|---|---|---|---|---|
| | 1-1 | 1-2 | 1-3 | 1-4 | 1-5 | 1-6 | 1-7 |
| Ratio of side flow withdrawal amount (%) | 24.4 | 48.6 | 72.7 | 78.8 | 84.9 | 90.8 | 0.0 |
| Top loss rate (%) | 4.53 | 4.56 | 4.59 | 4.59 | 4.60 | 4.60 | 4.50 |
| Ratio of dimer formation amount, relative to that of Experimental Example 1-7 (%) | 86.7 | 73.2 | 55.6 | 49.8 | 42.9 | 34.5 | 100 |

The acrylic acid concentration and dimer concentration of Experimental Example 1-7 shown by the mark "*" in Table 1 indicates the acrylic acid concentration and dimer concentration of the bottom liquid, respectively.

From the results of Table 1, it is understood that even if the crude acrylic acid solution is withdrawn as a side flow of the absorption tower, the crude acrylic acid solution having a concentration equal to or higher than that in cases where it is withdrawn as the bottom liquid can be obtained. The side flow of the absorption tower contains neither solid matter nor acrylic acid dimer, and therefore, filters for removing solid matter and steps of decomposing acrylic acid dimer can be omitted or simplified by employing the method of withdrawing the crude acrylic acid solution as a side flow of the absorption tower.

From the results of Table 1, it is further understood that in Experimental Examples 1-1 to 1-6, the acrylic acid dimer formation amount at the bottom portion can be decreased to 87% by mass or lower with an increase in the side flow withdrawal amount (i.e., Experimental Example 1-1, 0.117 kg/hour (86.7% of that in Experimental Example 1-7); Experimental Example 1-2, 0.099 kg/hour (73.2% of that in Experimental Example 1-7); Experimental Example 1-3, 0.075 kg/hour (55.6% of that in Experimental Example 1-7); Experimental Example 1-4, 0.067 kg/hour (49.8% ofthat in Experimental Example 1-7); Experimental Example 1-5, 0.058 kg/hour (42.9% in Experimental Example 1-7); and Experimental Example 1-6, 0.047 kg/hour (34.5% of that in Experimental Example 1-7)). In cases where the side flow withdrawal amount per unit time is greater than 8.0 kg/hour (96.9% by mass, relative to the total mass of the side flow and the bottom liquid, both of which were withdrawn from the absorption tower), the pipe at the bottom of the absorption tower caused clogging, thereby making it impossible to continue the operation of the absorption tower.

In other words, the acrylic acid dimer formation amount can be decreased by withdrawing the crude acrylic acid solution as a side flow of the absorption tower, as compared with the cases where the crude acrylic acid solution is withdrawn as the bottom liquid, and therefore, the loss rate of acrylic acid is small and acrylic acid can be obtained in high yield.

Experimental Example 2

In Experimental Example 2, the crude acrylic acid solution was withdrawn in the same manner as described in Experimental Example 1, except that the amount of the crude acrylic acid solution withdrawn as a side flow was set to be 6 kg and the position for withdrawing the crude acrylic acid solution was changed to any of the positions corresponding to from 28% to 89% of the total theoretical plate number, counted from the top portion to the bottom portion of the absorption tower, with the base point being on the top side of the absorption tower (referred to hereinafter as Experimental Examples 2-1 to 2-5).

The composition of the crude acrylic acid solution obtained and the composition of the bottom liquid of the absorption tower are shown, together with the positions of the withdrawal outlets, in Table 2. In Table 2, there are also shown the results of Experimental Example 1-7 in which the crude acrylic acid solution was withdrawn as the bottom liquid of the absorption tower.

TABLE 2

| | | Experimental Example | | | | | |
|---|---|---|---|---|---|---|---|
| | | 2-1 | 2-2 | 2-3 | 2-4 | 2-5 | 1-7 |
| Side flow | Plate number for withdrawal | 16 (89%) | 13 (72%) | 10 (56%) | 7 (39%) | 5 (28%) | — |
| | Acrylic acid concentration (%) | 92.75 | 91.30 | 90.98 | 90.41 | 89.50 | 92.40* |
| | Dimer concentration (%) | 0 | 0 | 0 | 0 | 0 | 1.65* |
| | Solid matter concentration (ppm) | 0 | 0 | 0 | 0 | 0 | — |
| Bottom liquid | Mass (kg/hour) | 2.25 | 2.28 | 2.22 | 2.06 | 1.82 | 8.19 |
| | Dimer mass (kg/hour) | 0.075 | 0.076 | 0.075 | 0.072 | 0.068 | 0.135 |

TABLE 2-continued

| | Experimental Example | | | | | |
|---|---|---|---|---|---|---|
| | 2-1 | 2-2 | 2-3 | 2-4 | 2-5 | 1-7 |
| Solid matter concentration (ppm) | 18 | 18 | 19 | 20 | 21 | 5 |
| Ratio of side flow withdrawal amount (%) | 72.23 | 72.46 | 72.99 | 74.44 | 76.73 | 0 |
| Top loss rate (%) | 4.53 | 5.11 | 6.12 | 8.39 | 11.95 | 4.50 |
| Ratio of dimer formation amount, relative to that of Experimental Example 1-7 (%) | 55.6 | 55.9 | 55.2 | 53.4 | 50.6 | 100 |

In Table 2, the numerical values described in the raw, described as "Plate number for withdrawal", indicate the theoretical plate numbers at the respective withdrawal outlets for the crude acrylic acid solution, and the numeral values in the parentheses indicate the ratios of the theoretical plate numbers for the respective withdrawal outlets to the total theoretical plate number, counted from the top portion to the bottom portion of the absorption tower, with the base point being on the top side of the absorption tower. In addition, the acrylic acid concentration and dimer concentration of Experimental Example 1-7 shown by the mark "*" in Table 2 indicates the acrylic acid concentration and dimer concentration of the bottom liquid, respectively.

From the results of Table 2, it is understood that there are tendencies that: with a decrease in the plate number at the withdrawal outlet for the crude acrylic acid solution (i.e., on the top portion side of the absorption tower), the formation amount of acrylic acid dimer is decreased, the acrylic acid concentration of the crude acrylic acid solution is also decreased, and the loss rate of the acrylic acid-containing gas from the top of the absorption tower is increased. It is further understood that the formation amount of acrylic acid dimer can be decreased by providing the withdrawal outlet for the crude acrylic acid solution between the supply point for the acrylic acid-containing gas and the supply point for the absorbent, as compared with the cases where the crude acrylic acid solution is withdrawn as the bottom liquid.

Experimental Example 3

Purification of Crude Acrylic Acid Solution

In this Experimental Example, 6 kg of the crude acrylic acid solution produced under the same conditions as used in Experimental Example 1-3 was purified by a method of purification by crystallization or by a method of purification by distillation.

Experimental Example 3-1

Method of Purification by Crystallization

Using a crystallization purifier in accordance with a crystallizer as disclosed in Japanese Patent Publication No. 53-41637, dynamic crystallization was carried out. The crystallization purifier comprises a metal tube of 6 m in length and 70 mm in inner diameter, provided with a reservoir at the lower portion thereof. Using a circulating pump, liquid in the reservoir can be transferred to the upper portion of the tube and then allowed to flow as a falling film on the inner wall of the tube. The outer wall of the tube comprises a double jacket which is controlled to have a constant temperature by thermostat. To this reservoir, the crude acrylic acid solution (composition: 92.75% by mass of acrylic acid, 4.99% by mass of water, 2.50% by mass of acetic acid, 0.16% by mass of other impurities) was supplied at a rate of 6 kg/hour, and dynamic crystallization was carried out according to the following procedures. The following procedures indicate one operation of dynamic crystallization.

1. Crystallization: The crude acrylic acid solution supplied to the reservoir was transferred to the upper portion of the tube by the circulating pump and then allowed to flow as a falling film on the inner wall of the tube. The temperature of the jacket is decreased to the freezing point of acrylic acid or lower, so that from about 60% by mass to 80% by mass of acrylic acid contained in the crude acrylic acid solution was crystallized on the inner wall of the tube.

2. Sweating: The circulating pump was stopped, and the temperature of the jacket was increased to around the freezing point of acrylic acid, so that from about 2% by mass to 5% by mass of the crystallized acrylic acid was sweated. After the sweating, the remaining crude acrylic acid solution and the sweated liquid were pumped out of the reservoir.

3. Melting: The temperature of the jacket was increased to the freezing point of acrylic acid or higher, so hat the crystals were melted into liquid acrylic acid, which was pumped out of the reservoir.

The above operation was repeated four times to obtain purified acrylic acid. In the above operation, the temperature and the freezing point of acrylic acid were allowed to depend upon the respective procedures.

According to the above operation of dynamic crystallization, acrylic acid having a purity of 99.91% by mass was obtained at a rate of 2.92 kg/hour. At this time, water and acetic acid contained in the acrylic acid crystals were at amounts of 248 ppm by mass and 602 ppm by mass, respectively.

Experimental Example 3-2

Method of Purification by Distillation

To a distillation tower having flat perforated trays corresponding to the theoretical plate number of 18 and having, at the top portion thereof, a recycling line for condensing condensable components in a gas discharged from the distillation tower and then introducing the resulting condensed liquid again to the absorption tower, the crude acrylic acid solution was supplied at a rate of 6 kg/hour, and the purification of acrylic acid was carried out. The distillation tower used in the this purification step was provided with a condenser at the top thereof, a supply inlet for the crude acrylic acid solution at a position corresponding to the theoretical plate number of 9 counted from the top portion thereof, a side flow withdrawal outlet and a condenser at a position corresponding to the theoretical plate number of 17 counted from the top portion thereof, and a reboiler at the bottom portion thereof.

From the crude acrylic acid solution supply inlet of the distillation tower, the crude acrylic acid solution (composition: 93.10% by mass of acrylic acid, 1.88% by mass of acetic acid, 4.87% by mass of water, 0.04% by mass of acrolein, and 0.11% by mass of others) was supplied at a rate of 6 kg/hour to the distillation tower, and from the reflux line at the top portion of the distillation tower, polymerization inhibitors (40 ppm by mass copper dibutyldithiocarbamate and 100 ppm by mass of phenothiazine; these amounts being relative to the amount of vaporized acrylic acid) were introduced into the distillation tower. At this time, in order that the operating pressure at the top of the distillation tower became 100 hPa (absolute pressure) the pressure in the distillation tower was decreased by a steam ejector, and a control valve between the side flow withdrawal outlet and a vacuum apparatus provided downstream the withdrawal outlet was adjusted to control a differential pressure between the side portion and the top portion of the distillation tower at 95 hPa, so that the ratio of the amount of vapor withdrawn from the side flow withdrawal outlet and the flow amount of distillate liquid discharged from the top portion of the distillation tower became 4:1. Further, the bottom liquid of the distillation tower was withdrawn at a rate of 0.8 kg/hour, and the vapor of purified acrylic acid was obtained at a rate of 4.3 kg/hour from the side flow withdrawal outlet of the distillation tower. At this time, the vapor of acrylic acid was supplied by the reboiler provided at the bottom of the distillation tower to control the bottom liquid surface, so that the reflux ratio in the distillation tower was set to be 3.4.

The purified acrylic acid obtained at this time had a purity of 99.82% and contained, as impurities, 100 ppm by mass of water, 1,300 ppm by mass of acetic acid, 1 ppm by mass or lower (detection limit) of acrolein, and 400 ppm by mass of others.

From the results of Experimental Example 3, it is understood that high purity acrylic acid can be obtained with high efficiency, regardless of the kind of purification method, by employing the production process of the present invention in which a crude acrylic acid solution is withdrawn from the withdrawal outlet positioned between the supply point for the acrylic acid-containing gas and the supply point for the absorbent in the absorption step.

Experimental Example 4

Decomposition Step

The distillation of the bottom liquid containing high boiling point components obtained under the same conditions as used in Experimental Example 3 and the decomposition of Michael adducts were carried out to recover acrylic acid.

Experimental Example 4-1

Step Provided with Tower for Separating High Boiling Point Components in Addition to Thin Film Evaporator and Thermal Decomposition Tank The bottom liquid of the absorption tower (composition: 87.7% by mass of acrylic acid, 2.0% by mass of water, 1.1% by mass of acetic acid, 1.5% by mass of maleic acid, 6.2% by mass of acrylic acid dimer, 1.5% by mass of other impurities) was supplied at a rate of 2.25 kg/h (acrylic acid dimer, 0.075 kg/h) to the middle plate of a distillation tower (i.e., a tower for separating high boiling point components) provided with sieve trays corresponding to the theoretical plate number of 20 and a reboiler. At this time, the distillation tower was controlled under the conditions that the operation pressure was 93 hPa and the reflux ratio was 0.3. In the thermal decomposition tank, the thermal decomposition of Michael adducts was carried out under the conditions that the temperature of the thermal decomposition tank was 170° C. and the retention time was 30 hours. The thin film evaporator was controlled so that the bottom temperature became 95° C., and acrylic acid was recovered under the conditions that the pressure at the top thereof was 33 hPa and the reflux ratio was 1.5. At this time, the conversion rate of Michael adducts was 65% and the selectivity to acrylic acid was 75%, and 48.8% (0.037 kg/h) of acrylic acid was able to be recovered from the acrylic acid dimer.

Experimental Example 4-2

Step Employing Reactive Distillation System

In the step of decomposing Michael adducts, the same operation as used in Experimental Example 4 was carried out, except that a reactive distillation apparatus provided with a forced-circulation type external heat exchanger as shown in FIG. 2 was used. The reactive distillation apparatus was carried out for the thermal decomposition of Michael adducts under the conditions that the thermal decomposition temperature was 170° C., the retention time was 4 hours, and the pressure was 266 hPa. At this time, the conversion rate of Michael adducts was 82% and the selectivity to acrylic acid was 98%, and 80.4% (0.060 kg/h) of acrylic acid was able to be recovered from the acrylic acid dimer.

From the results of Experimental Example 4, it is understood that for the purpose of recovering acrylic acid with high efficiency from the bottom solution of the absorption tower, the step employing the reactive distillation system is preferred to the step provided with a tower for separating high boiling point components in addition to a thin film evaporator and a thermal decomposition tank.

The invention claimed is:

1. A process for producing (meth)acrylic acid comprising an absorption step of bringing a (meth)acrylic acid-containing gas obtained by a gas phase catalytic oxidation method into an absorption tower and allowing the gas to contact with an absorbent, thereby absorbing the (meth)acrylic acid as a crude (meth)acrylic acid solution, in which absorption step the crude (meth)acrylic acid solution is withdrawn from a withdrawal outlet positioned between a supply point for the (meth)acrylic acid-containing gas and a supply point for the absorbent on the absorption tower, and then supplied to a next step.

2. The process for producing (meth)acrylic acid according to claim 1, wherein a (meth)acrylic acid concentration in the crude (meth)acrylic acid solution withdrawn from the absorption tower is 80% by mass or higher.

3. The process for producing (meth)acrylic acid according to claim 1, wherein the next step is a step of separation and purification of (meth)acrylic acid from the crude (meth)acrylic acid solution.

4. The process for producing (meth)acrylic acid according to claim 3, wherein the step of separation and purification comprises a crystallization step and/or a distillation step.

5. The process for producing (meth)acrylic acid according to claim 1, wherein the absorbent comprises water.

* * * * *